US008568489B2

(12) United States Patent
Finlinson et al.

(10) Patent No.: US 8,568,489 B2
(45) Date of Patent: Oct. 29, 2013

(54) VACUUM PUMP FOR A PROSTHETIC DEVICE

(75) Inventors: Robert Edward Finlinson, Salt Lake City, UT (US); Douglas E. Rush, Draper, UT (US); Lüder Mosler, Duderstadt (DE)

(73) Assignee: Otto Bock Healthcare LP, Minneapolis, MN (US)

( * ) Notice: Subject to any disclaimer, the term of this patent is extended or adjusted under 35 U.S.C. 154(b) by 309 days.

(21) Appl. No.: 12/184,329

(22) Filed: Aug. 1, 2008

(65) Prior Publication Data

US 2009/0036998 A1 Feb. 5, 2009

Related U.S. Application Data

(60) Provisional application No. 60/953,400, filed on Aug. 1, 2007.

(51) Int. Cl.
*A61F 2/60* (2006.01)

(52) U.S. Cl.
USPC ................................ 623/27; 623/33; 417/480

(58) Field of Classification Search
USPC .......... 417/478, 472, 148; 623/34, 27, 32, 33, 623/35, 37
See application file for complete search history.

(56) References Cited

U.S. PATENT DOCUMENTS 2,696,011 A 12/1954 Galdik
4,091,471 A * 5/1978 Richter ........................ 623/3.21
5,133,776 A 7/1992 Crowder
5,201,774 A 4/1993 Greene
5,258,037 A 11/1993 Caspers
5,458,656 A 10/1995 Phillips
5,658,353 A 8/1997 Layton
5,702,489 A 12/1997 Slemker (Continued)

FOREIGN PATENT DOCUMENTS

CA 2574889 2/2006
DE 745981 * 3/1944

(Continued)

OTHER PUBLICATIONS

Article: "Harmony Instructions for Use", Otto Bock HealthCare product brochure at www.ottobock.com, dated Mar. 2004; 13 pgs.

(Continued)

*Primary Examiner* — David Isabella
*Assistant Examiner* — Marcia Hoffman
(74) *Attorney, Agent, or Firm* — Holland & Hart

(57) ABSTRACT

The present invention in one embodiment is a vacuum pump including a compressible elastomeric member with an internal reservoir enclosing a volume of fluid, an outlet port providing fluid communication between the internal reservoir and a fluid sink, and an inlet port providing fluid communication between the internal reservoir and a fluid source. The pump further includes first and second pressure elements coupled to the elastomeric member on opposing sides. At least one of the first and second pressure elements is adapted to apply a longitudinal force along, and a rotational force about, an axis extending through the compressible elastomeric member. Upon the application of a longitudinal compression force to the compressible elastomeric member, fluid flows from the internal reservoir to the fluid sink and upon the application of a longitudinal expansion force, fluid flows from the fluid source to the internal reservoir. Upon the application of a rotational force, the elastomeric member exerts a counter-rotational force.

13 Claims, 17 Drawing Sheets

(56) References Cited

U.S. PATENT DOCUMENTS

| | | | | |
|---|---|---|---|---|
| 5,800,562 | A | 9/1998 | Wilkinson | |
| 5,888,214 | A | 3/1999 | Ochoa | |
| 5,904,721 | A | 5/1999 | Henry et al. | |
| 6,004,116 | A * | 12/1999 | Wang | 417/480 |
| 6,063,125 | A | 5/2000 | Arbogast et al. | |
| D429,335 | S | 8/2000 | Caspers et al. | |
| 6,117,177 | A | 9/2000 | Chen et al. | |
| 6,287,345 | B1 | 9/2001 | Slemker et al. | |
| 6,302,918 | B1 | 10/2001 | Gramnas | |
| 6,395,039 | B1 | 5/2002 | Thorn | |
| 6,468,315 | B1 | 10/2002 | Wilkinson et al. | |
| 6,478,826 | B1 | 11/2002 | Phillips et al. | |
| 6,511,512 | B2 | 1/2003 | Phillips et al. | |
| 6,554,868 | B1 | 4/2003 | Caspers | |
| 6,645,253 | B2 | 11/2003 | Caspers | |
| 6,682,569 | B2 | 1/2004 | Wilkinson et al. | |
| 6,726,726 | B2 | 4/2004 | Caspers | |
| 6,761,742 | B2 | 7/2004 | Caspers | |
| 6,827,343 | B2 | 12/2004 | Skiera | |
| 6,877,965 | B2 | 4/2005 | McCall et al. | |
| 6,887,279 | B2 | 5/2005 | Phillips et al. | |
| 6,926,742 | B2 | 8/2005 | Caspers et al. | |
| 6,969,408 | B2 | 11/2005 | Lecomte et al. | |
| 7,025,792 | B2 | 4/2006 | Collier | |
| 7,169,190 | B2 | 1/2007 | Phillips et al. | |
| 7,228,923 | B2 | 6/2007 | Takenaka et al. | |
| 7,371,262 | B2 | 5/2008 | Lecomte et al. | |
| 2001/0016781 | A1 | 8/2001 | Caspers | |
| 2003/0191539 | A1 | 10/2003 | Caspers | |
| 2004/0143345 | A1 | 7/2004 | Caspers | |
| 2004/0181290 | A1 | 9/2004 | Caspers | |
| 2005/0131511 | A1 | 6/2005 | Westlund | |
| 2005/0197611 | A1 | 9/2005 | Taranow | |
| 2005/0209707 | A1 * | 9/2005 | Phillips et al. | 623/35 |
| 2005/0240282 | A1 | 10/2005 | Rush et al. | |
| 2006/0212130 | A1 * | 9/2006 | Collier | 623/26 |
| 2007/0019622 | A1 | 1/2007 | Alt et al. | |
| 2007/0196222 | A1 | 8/2007 | Mosler et al. | |
| 2009/0299491 | A1 | 12/2009 | Slemker et al. | |

FOREIGN PATENT DOCUMENTS

| | | | |
|---|---|---|---|
| DE | 745981 | | 5/1944 |
| DE | 002060239 | * | 12/1970 |
| DE | 002540138 | * | 9/1975 |
| DE | 2729800 | | 1/1979 |
| WO | 8400881 | | 3/1984 |
| WO | 0170147 | | 9/2001 |
| WO | WO 2006/012820 | | 2/2006 |
| WO | WO 2009/015896 | | 2/2009 |

OTHER PUBLICATIONS

Article: “Harmony Restoring Human Independence”, Otto Bock HealthCare product brochure at www.ottobock.com, dated Sep. 2004, 2 pgs.

Article: “Harmony P2 and Harmony HD—Introducing the new Harmony P2 from Otto Bock:”, Otto Bock HealthCare product brochure at www.ottobock.com, dated 2004, 2 pgs.

Article: “The Harmony Volume Management System Component Selection Chart”, Otto Bock product brochure at www.ottobock.com dated Mar. 2005, 1 pg.

Article: “4R146=RPA Harmony DP Instructions for Use”, Otto Bock HealthCare product brochure fat www.ottobock.com, dated Dec. 2004, 1 pg.

Article: “A Comparison of trans-tibial amputee suction and vacuum socket conditions”, W.J. Board, et al, Prosthetics and Orthotics International, 2001, 25, 202-209, pp. 202-208.

Article: “Interface pressures during ambulation using suction and vacuum-assisted prosthetic sockets”, Department of Veterans Affairs, Journal of Rehabilitation Research and Development, vol. 39, No. 6, Nov./Dec. 2002, pp. 693-700, Tracy L. Beil, et al.

Article: “Walking in a vacuum-assisted socket shifts the stump fluid balance”, Prosthetics and Orthotics International, 2003, 23, 107-113, J. Goswami, et al.

Product Information: Otto Bock Delta Twist Shock Absorber, printed Apr. 22, 2004, 2 pgs.

* cited by examiner

VACUUM PUMP FOR A PROSTHETIC DEVICE

CROSS-REFERENCE TO RELATED APPLICATION

This application claims the benefit under 35 U.S.C. §119 (e) of Provisional Application No. 60/953,400, filed Aug. 1, 2007, which is herein incorporated by reference in its entirety.

TECHNICAL FIELD

The present invention relates generally to prosthetic devices, and more particularly to vacuum pumps used to generate a vacuum attachment of the prosthetic device to the residual limb of a user.

BACKGROUND

An ongoing challenge in the development of prosthetic limbs is the attachment of the prosthetic limb to the residual limb of a user. For prosthetic legs, it is often difficult to securely attach the prosthetic leg to the residual leg without exerting too much or uneven pressure on the residual limb. On the one hand, the lack of a secure attachment can adversely affect the user's ability to walk. On the other hand, an improper fit can cause sores, swelling and pain for the user.

One approach for overcoming this challenge has been the application of a negative pressure vacuum in a space between the limb (or a liner donned on the limb) and a socket or receptacle coupled to the prosthetic limb (see FIG. 1 generally). Two conventional ways to apply such a vacuum are by a mechanical pump or an electronic pump.

Mechanical pumps are often in-line systems that utilize the movement of the user to generate the negative pressure vacuum in the socket. For example, the force generated by contacting the ground during a user's walking motion can be used to generate a vacuum in the socket space to hold the prosthesis to the user's limb. However, in utilizing the motion of the user, such pumps should not inhibit, and should ideally aid in, as natural and pain-free of a movement as possible for the user.

SUMMARY

One embodiment of the present invention provides a vacuum pump including a compressible elastomeric member. The compressible elastomeric member includes an internal reservoir enclosing a volume of fluid, an outlet port providing fluid communication between the internal reservoir and a fluid sink, and an inlet port providing fluid communication between the internal reservoir and a fluid source. The pump further includes first and second pressure elements coupled to the elastomeric member on opposing sides.

At least one of the first and second pressure elements is adapted to apply a longitudinal force along, and a rotational force about, an axis extending through the compressible elastomeric member. Upon the application of a longitudinal compression force to the compressible elastomeric member, fluid flows from the internal reservoir to the fluid sink and upon the application of a longitudinal expansion force, fluid flows from the fluid source to the internal reservoir. Upon the application of a rotational force, the elastomeric member exerts a counter-rotational force. The inlet may be attached to an enclosed space such that upon the application of the expansion force, a negative pressure vacuum is applied to the enclosed space.

Another embodiment of the present invention provides a prosthetic device for attachment to a residual limb. The prosthetic device includes a vacuum pump having a compressible elastomeric member including an internal reservoir enclosing a volume of fluid, an outlet port providing fluid communication between the internal reservoir and a fluid sink and an inlet port providing fluid communication between the internal reservoir and a fluid source. The prosthetic device also includes a first support member having a proximal end configured for attachment to the residual limb and a distal end coupled to a first side of the elastomeric housing, and a second support member having a proximal end coupled to a second opposing side of the elastomeric member.

One or both of the first and second support members are adapted to apply a longitudinal force along, and a rotational force about, an axis extending through the compressible elastomeric member. Upon the application of a longitudinal compression force to the compressible elastomeric member, fluid flows from the internal reservoir to the fluid sink and upon the application of a longitudinal expansion force, fluid flows from the fluid source to the internal reservoir. Additionally, upon the application of a rotational force the elastomeric member exerts a counter-rotational force. The fluid source may be an enclosed space formed between the residual limb of a user and a receptacle attached to the upper support, such that a negative pressure vacuum is formed in the enclosed space to maintain the attachment of the prosthesis.

A further embodiment of the present invention provides a leg prosthesis for attachment to a residual portion of a leg. The leg prosthesis includes a receptacle for receiving the limb, a foot portion and a vacuum pump. The vacuum pump includes a housing having an interior compartment and a shaft member having a portion disposed in the interior compartment of the housing. The housing and shaft member are coupled to provide reciprocating movement along a longitudinal axis extending through the housing and shaft member.

The vacuum pump further includes a compressible elastomeric member having an internal reservoir enclosing a volume of fluid, an outlet port providing fluid communication between the internal reservoir and a fluid sink and an inlet port providing fluid communication between the internal reservoir and a fluid source. Upon the application of a compression force along the longitudinal axis, the shaft moves relative to the housing to compress the elastomeric member such that fluid flows from the internal reservoir to the fluid sink, and upon the application of an expansion force, the shaft moves relative to the housing to expand the elastomeric member such that fluid flows from the fluid source to the internal reservoir.

Yet another embodiment of the present invention provides a foot prosthesis including an upper plate configured for attachment to a lower leg prosthesis or residual limb and a lower plate adapted to contact a walking surface. The upper plate extends between an ankle portion and a toe portion and the lower plate extends between a heel portion and a toe portion. The lower and upper plates are coupled such that a space is defined between the ankle portion and the heel portion. Upon the application of a compression force to the ankle portion or heel portion, the space is reduced.

The foot prosthesis also includes a vacuum pump disposed in the space between the ankle and heel portions. The vacuum pump includes an elastomeric member with an internal reservoir adapted to enclose a volume of fluid, an outlet port in fluid communication with the internal reservoir and a fluid sink, and an inlet port in fluid communication with the internal reservoir and a fluid source. Upon the application of the compression force the elastomeric member compresses such that fluid flows from the reservoir to the fluid sink, and wherein upon the termination of the compression force, the upper or lower plate cause the application of an expansion force to the elastomeric member such that fluid flows from the fluid source into the reservoir.

A further embodiment provides a vacuum pump including an elongated upper pylon and an elongated lower pylon adapted to move axially and rotationally with respect to said upper pylon, wherein the longitudinal axis of the upper pylon and the longitudinal axis of the lower pylon are maintained in a generally colinear alignment. The vacuum pump further includes a resilient compressible elastic member coupled to and disposed between respective ends of the upper and lower pylons to resist the axial and rotational movement of the lower pylon The elastic member includes an internal reservoir enclosing a volume of fluid, which may be formed by a substantially continuous elastic wall enclosing the internal reservoir.

An outlet port provides fluid communication between the internal reservoir and a fluid sink and an inlet port providing fluid communication between the internal reservoir and a fluid source. Upon the application of a compression force along the longitudinal axis, the upper pylon moves relative to the lower pylon to compress the elastomeric member such that fluid flows from the internal reservoir to the fluid sink. Upon the application of an expansion force, the upper pylon moves relative to the lower pylon to expand the elastomeric member such that fluid flows from the fluid source to the internal reservoir.

The present invention also provides methods of using the vacuum pump described above to apply a vacuum to a space between a user's residual limb and a receptacle of a prosthetic device. While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

DETAILED DESCRIPTION

Various modifications and additions can be made to the exemplary embodiments discussed below without departing from the scope of the present invention. For example, while the embodiments described below refer to particular features, the scope of this invention also includes embodiments having different combinations of features and embodiments that do not include all of the above described features.

Figure 1:
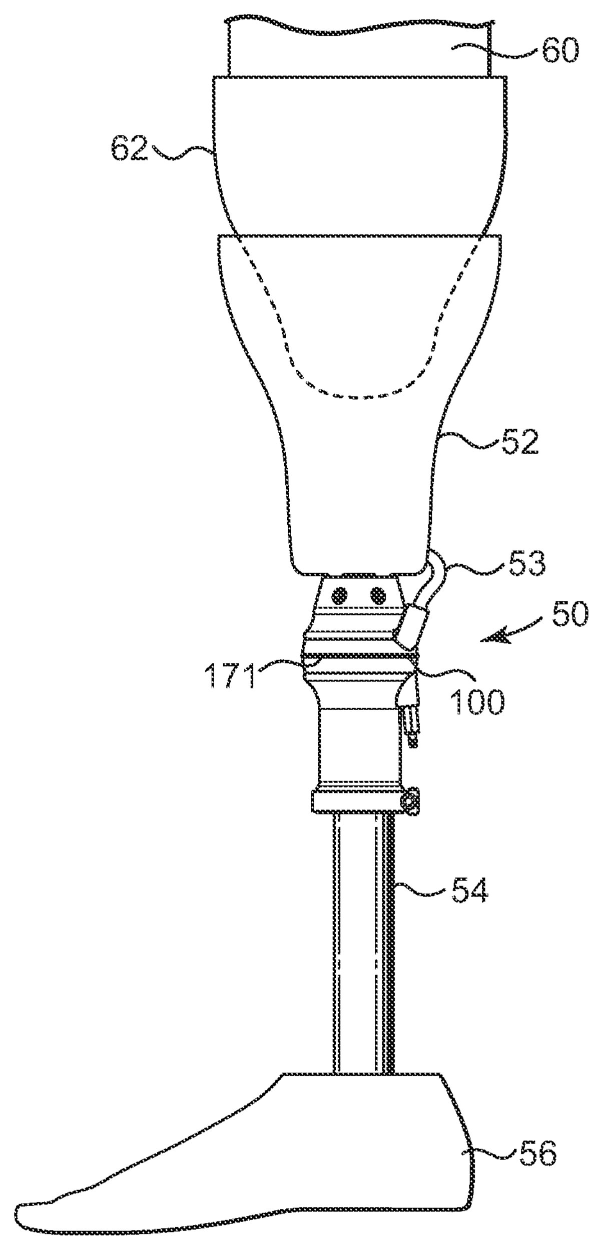
FIG. 1 shows an artificial limb engaged with a residual limb and including a socket, vacuum pump, pylon and prosthetic foot.

One embodiment of the present invention is a vacuum pump that can be used with an artificial limb, such as an artificial leg, artificial arm or other prosthetic device. FIG. 1 shows an artificial leg 50 including a socket 52 coupled to one end of a pylon 54 via a vacuum pump 100 in accordance with the present invention. An artificial foot 56 is coupled to the other end of the pylon 54. A residual limb, or residuum 60, of a user is encased in a liner 62 and is received within the socket 52 that has been configured in size and shape to accept the residuum 60. A fluid connection, such as tube 53, connects the vacuum pump 100 to a space formed between the socket 52 and the liner 62 and/or residuum 60 when the artificial leg is attached.

As further shown in FIGS. 1-7, the vacuum pump 100 includes a shaft or upper pylon 120 with an end attachment 130; a housing or lower pylon 140 and a hollow, elastomeric structure 160 that is shaped like a toroid. The hollow elastomeric structure 160, hereinafter referred to as the toroid 160, is interposed or sandwiched between the end attachment 130 and the housing 140, with the shaft 120 passing through a central opening 170 of the toroid 160. As further shown in FIG. 6-7, the toroid 160 includes two generally flat top and bottom surfaces 161 and two outwardly bowed side walls 163 defining an internal reservoir 162.

When the pump 100 is compressed by an external force along a longitudinal axis extending through the pump, such as during the step phase of the user, the toroid 160 is compressed and a substantial volume of the fluid within its internal reservoir 162 is forced out through an outlet 164 to a fluid sink, which may be an external fluid atmosphere. When the external force on the pump 100 lessens or is removed, the elastomeric material, and particularly the side wall 163, of the toroid 160 causes the toroid 160 to return or expand back to its initial configuration due to its elastic memory and/or resiliency. As a result, the toroid 160 draws fluid from a fluid source into the internal cavity 162 through an inlet 166. An outlet check valve 165, such as a one-way expulsion valve, and a one-way intake check valve 167, can be connected to the internal cavity 162 at the outlet 164 and the inlet 166, respectively.

When the intake valve 167 is connected to a vessel, such as the space adjacent to socket 52, fluid is evacuated from the vessel/socket 52 by the pump 100. Since the residuum 60 and liner 62 are substantially sealed to the socket 52 about the periphery of the residuum 60, evacuation of fluid from the sealed socket 52 results in negative pressure or a vacuum being formed in the socket 52 about the residuum 60. As a result, the pump 100, functions as a vacuum pump that holds the socket 52 to the liner 62 and/or residuum 60. In this manner, the vacuum pump 100 removes the fluid, in this case air (which may include moisture from the limb), from the space between the prosthetic liner 62 and the socket 52 after placement of the residuum 60 and liner 62 within the socket 52. The socket 52 can also be arranged so that fluid is removed from between the liner 62 and skin of the residuum 60, which would further facilitate removal of perspiration.

In an artificial limb, such as the limb 50 shown in FIG. 1, the compression force results from the weight of the user being transmitted through the residuum 62. In a standing position, the weight of the user is distributed between the artificial limb 50 and the user's other lower limb. However, when the user takes a step while walking, the majority of the weight is placed onto the limb 50 as it engages the ground at the foot 56. The force continues until toe-off, when the foot 56 is lifted from the ground. The force remains removed through a swing phase, as the limb 50 is swung forward for another step. The compression force is then reapplied to the limb 50 and the pump 100 upon contact of the foot 56 to the ground. Thus, as the user walks, the compression force is repeatedly applied to and removed from the toroid 160 in a reciprocating manner. This process results in a generally continuous draw of fluid from the socket 52 creating the advantageous vacuum in the socket 52, as described above, which is particularly useful during the swing phase to maintain the attachment between the limb 50 and the socket 52.

Besides aiding in the retention of the artificial leg 50 on the residuum 60, removal of the fluid from between the socket 52 and liner 62 increases the intimacy of the socket fit, improving the user's ability to feel shock waves passed through the prosthetic structure, or artificial leg 50, and into the residuum 60. This can result in a "feeling" sensation and in increased awareness as to the location of the artificial leg 50 under the user. Although the fluid described with respect to FIG. 1 is air, fluid may mean any appropriate type of gas, including oxygen, nitrogen or air, with or without the addition of moisture.

The elastomeric toroid 160 is preferably formed from an elastomeric material, including but not limited to thermoset urethane, thermoplastic urethane or other suitable elastomers. In one embodiment, the toroid 160 is molded from a thermoset urethane in two halves that are bonded together to form an air-tight seal 171 around the circumference of outer wall 163 and a similar seal (not shown) along the circumference of inner wall 163. Other than the seals formed during production, the toroid 160, the inner and outer wall 163 form a substantially continuous elastomeric wall enclosing the internal reservoir 162.

In one embodiment the toroid 160 has an outer diameter of about 2.00 to 2.50 inches and an inner diameter of about 1.00 to about 1.50 inches, more particularly, about 1.13 inches. The wall thickness is about 0.10 to about 0.20 inches, more particularly, about 0.13 inches thick. The wall thicknesses of the toroid 160 determine its compression and expansion properties, as well as its rotational resilience about the longitudinal access extending through the pump 100, which is discussed in greater detail below. The rotational resilience is dependent primarily on the outer wall thickness, and the compression/expansion resilience is dependent primarily on the total wall thickness.

Figure 2:
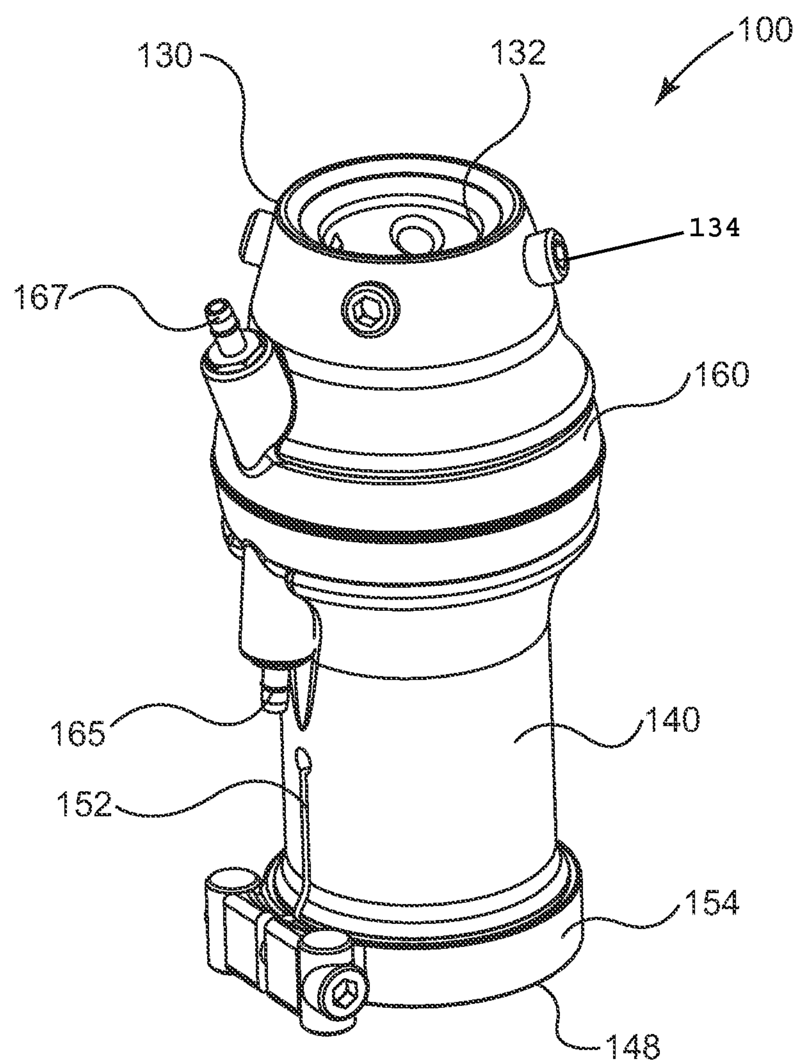
FIG. 2 shows a vacuum pump according to a first embodiment of the present invention.
Figure 3:
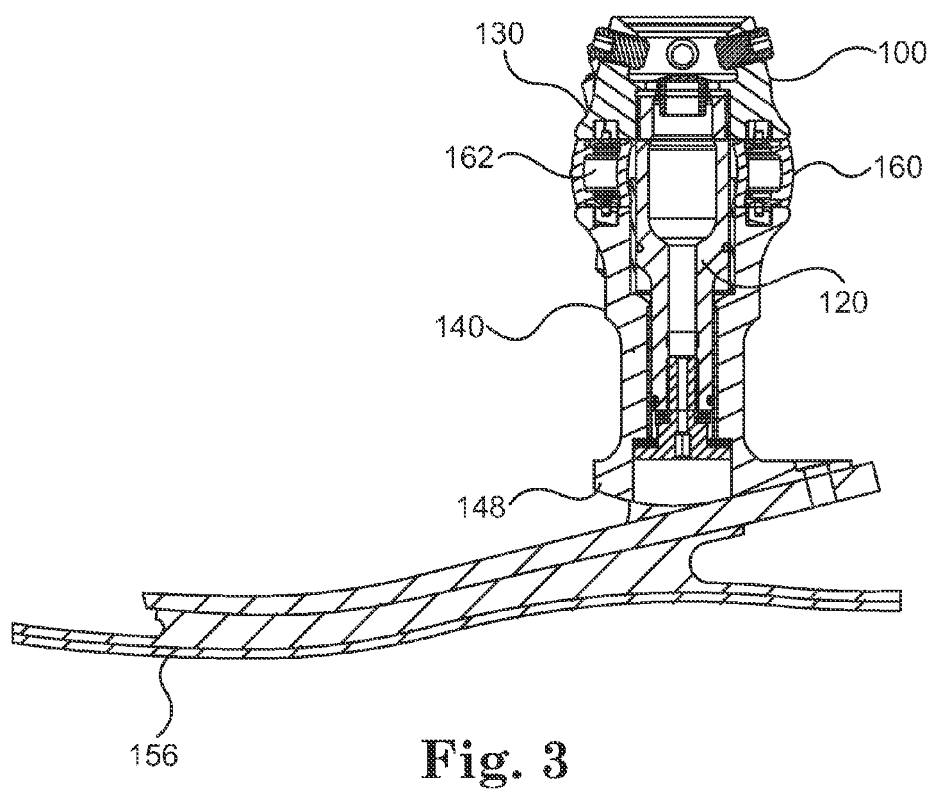
FIG. 3 shows a cross-section of the vacuum pump of FIG. 1 attached to a prosthetic foot.
Figure 4:
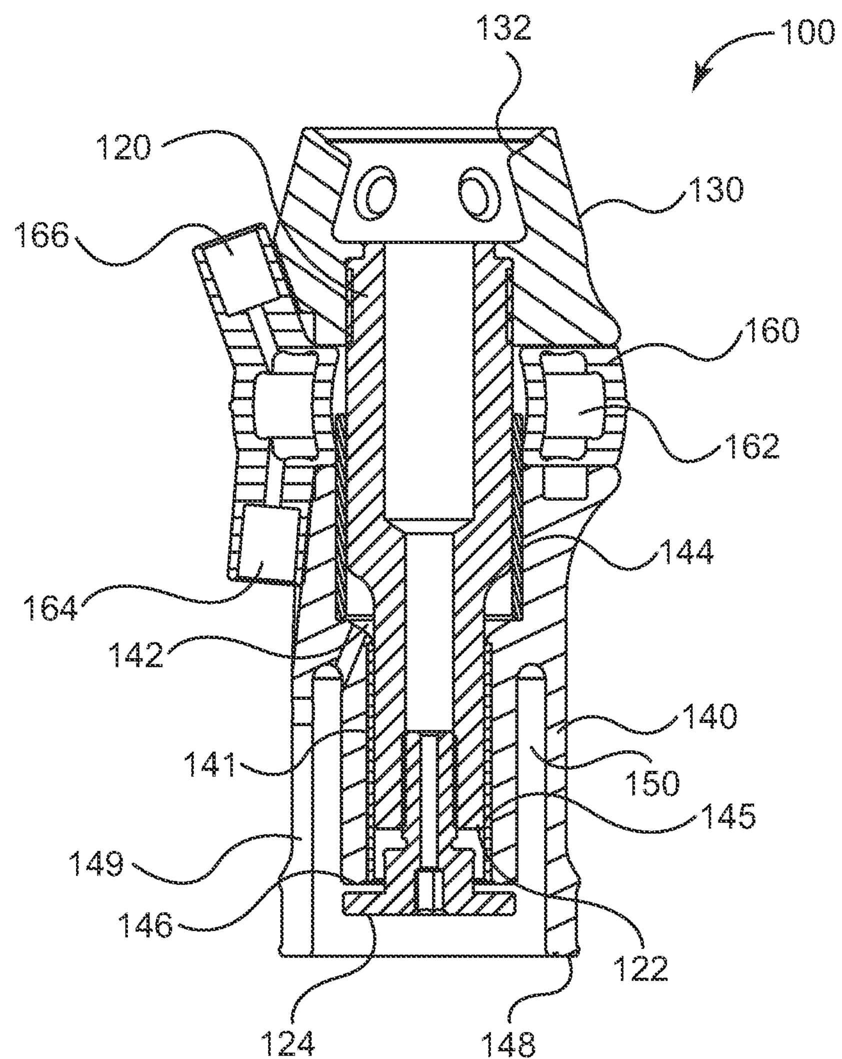
FIG. 4 shows another cross-section of the vacuum pump of FIG. 1.

In the embodiment shown in FIGS. 1-7, and more particularly in FIG. 4, the shaft 120 is received within the housing 140 in a compartment 142. The shaft 120 and the compartment 142 are preferably sized and shaped in a complementary manner, such that the shaft 120 smoothly rides axially within the compartment 142 as the compressive force is applied and removed. Bearings 144, 145 are provided to facilitate the smooth movement of the shaft 120, with bearings 144 provided within the compartment 142 and bearings 145 embedded within an inner wall 141 of the housing 140 adjacent to the compartment 142. A fastener 124 attaches to the shaft 120 at an end 122 opposite the end attachment 130. This fastener 124, such as a screw with a wide head shown in FIG. 4, engages an interior portion 146 of the housing 140 to restrict the movement of the shaft 120 and keep it in the interior compartment 142.

At the other end of the shaft 120, the end attachment 130 moves with the shaft 120 as it moves within the compartment 142. The end attachment 130 includes a mounting structure 132 configured for attachment to another prosthetic component using a prosthetic coupler, including but not limited to a pyramid connector (not shown). The mounting structure 132 includes a plurality of screws 134 for securing the pump 100 to the other prosthetic component, for example, a socket, a pylon, a foot and/or any other suitable component.

Figure 5:
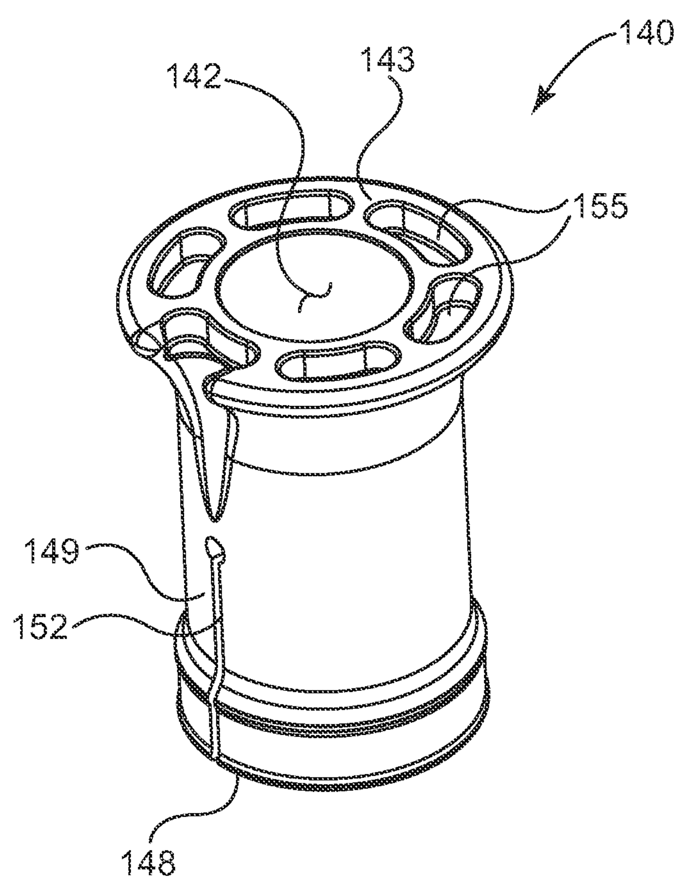
FIG. 5 shows a lower support portion of the vacuum pump of FIG. 1.
Figure 6:
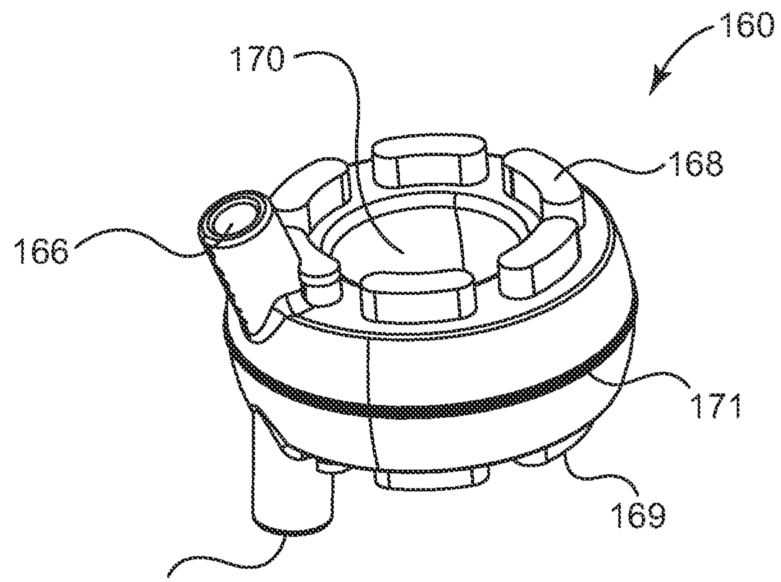
FIG. 6 shows a resilient portion of the vacuum pump of FIG. 1.
Figure 7:
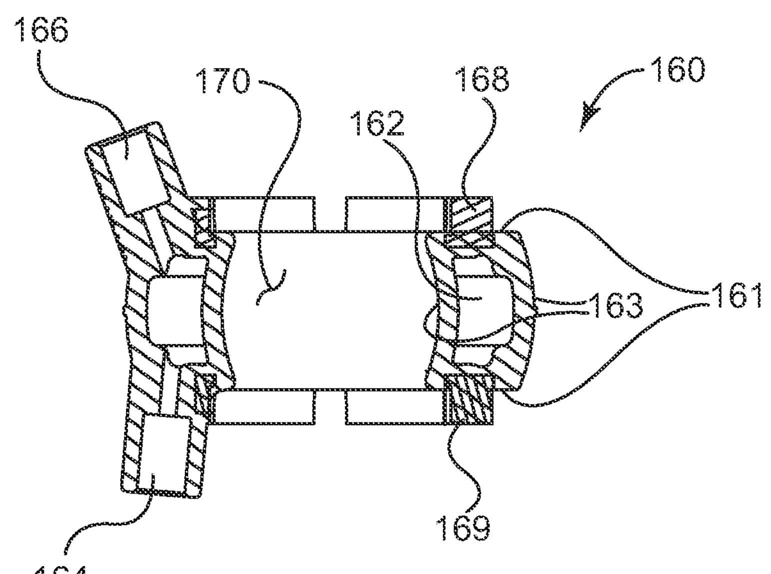
FIG. 7 shows a cross-section of the resilient portion shown in FIG. 6.

The housing 140 is also configured for connection to another prosthetic component. As shown in FIGS. 2, 4 and 5, the housing end 148 opposite from the toroid 160 is configured to be clamped to another prosthetic component, especially one having a pipe or pylon-type end. The housing 140 includes a cylindrical recess 150 sized and shaped to receive the pipe end. A split 152 in the housing wall 149 works with a clamp 154 to provide for a secure attachment of the housing 140 to the component. In FIG. 3, The housing 140 is shown with the end 148 formed for direct attachment to a prosthetic foot 156. In this manner, the need for additional coupling components is removed and the overall weight and height of the artificial limb may be reduced.

The prosthetic end attachments of the pump 100 can vary significantly depending on the components to which the pump 100 is intended to be attached. However, the current tube clamp in the housing is a space efficient design which allows a continuous length adjustment by cutting the attachment tube to the correct length.

In the embodiment shown in FIGS. 1-7, the pump 100 is not only designed to pump fluid and/or generate vacuum due to the application and removal of axial compressive forces, but it also provides shock absorption to the artificial limb and/or rotational resistance between the shaft 120 and the housing 140. In particular, the toroid 160 acts as a compression spring, a torsion spring, and as a vacuum generating device. With the toroid 160 sandwiched between the upper components of the artificial limb and the lower components of the limb, the elastomeric material helps absorb shocks due to impacts or other sharp forces. As a result, these forces are reduced and softened for the user and the artificial limb.

The toroid 160 is provided with a plurality of protrusions, such as torsion ribs 168, 169 extending from both surfaces of the toroid. One set of protrusions 168 engage or interlock with recesses or grooves (not shown) in the end attachment 130, which are sized and shaped to receive the ribs 168. In a similar manner, the other set of torsion ribs 169 engage with openings or grooves 155 formed in the top surface 143, or toroid end, of the housing 140. These torsion ribs 168, 169 keep the end attachment 130 and the housing 140 from rotating independently. However, when a torsional force is applied to the artificial limb, the components connected to the pump 100 at the end attachment 130 can twist relative to the components connected to the pump 100 at the housing 140. The resilient, elastomeric material of the toroid 160 allows for the twisting motion and also returns the components to their initial alignment upon withdrawal of the torsional force. In one embodiment, the toroid 160 provides gradually increasing resistance to the rotation. This ability also increased the comfort and usability of the artificial limb for the user. The amount of rotation can be controlled by the geometry of the ribs 168, 169 and toroid 160, or by the material and/or durometer of the toroid 160.

The pump 100 in accordance with the present invention has significant advantages over previous pump designs. One advantage is the small number of parts required, which means that the pump is more simple and cost effective to manufacture, and service. Another advantage is that the fluid passing through the pump is only in contact with the interior of the toroid 160 and the check valves 165, 167. The toroid 160 is constructed of an elastomer which has excellent corrosion resistance. Thus, the design can pump corrosive fluids without significant deleterious effects. In the example shown in FIG. 1, not only will air be drawn from the socket 52 into the internal cavity 162 of the toroid 160, but also moisture, such as perspiration, which is corrosive.

Figure 8:
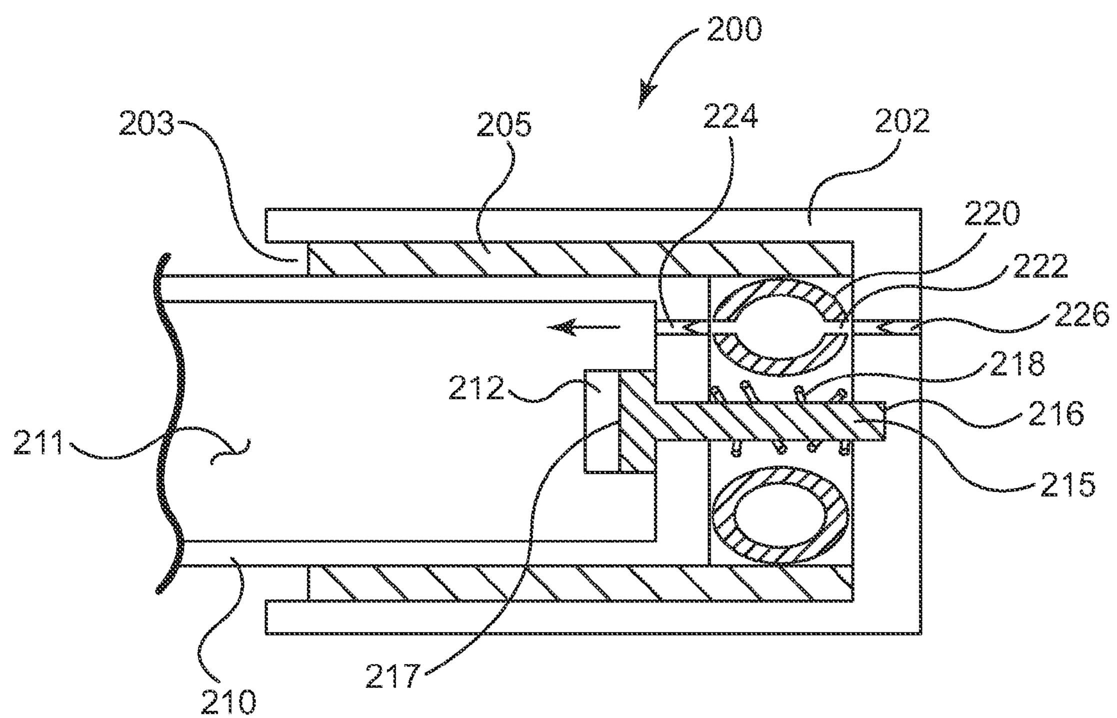
FIG. 8 shows a partial cross-section of a vacuum pump according to a second embodiment of the present invention.

The pump 200 shown in FIG. 8 is similar in operation to the pump 100 shown in FIGS. 1-7, except that the pump 200 includes a toroid 220 positioned within an interior compartment 203 of a housing 202. A hollow shaft 210 is also received within the housing 202 and positioned adjacent to the toroid 220. The shaft 210 reciprocates within the interior compartment 203 along a bushing 205 and a post 215 that passes through an end of the shaft 210 and is positioned through a center of the toroid 220. The post 215 is attached to the housing 202 at a first end 216 and a second end 217 is positioned within a compartment 212 in the interior 211 of the shaft 210. A spring 218 is positioned about the post 215 for applying a return force upon compression of the toroid 220. A one-way valve 222 extends through the toroid 220. Upon application of a compression force, the shaft 210 moves toward the toroid 220, compressing the toroid 220 and the spring 218. The compartment 212 moves relative to the second end 217 of the post 215. As the toroid compresses, fluid is transferred through an outlet 224 into the interior compartment 211. Upon reduction or removal of the compression force, fluid is drawn into the toroid 220 through an inlet 226 as the spring 218 returns the shaft 210 to its initial position. As stated above, if the inlet 226 is fluidly connected to a sealed vessel/socket, the pump 200 may be used to apply a vacuum within the prosthetic socket, as discussed with respect to FIGS. 1-7.

Figure 9:
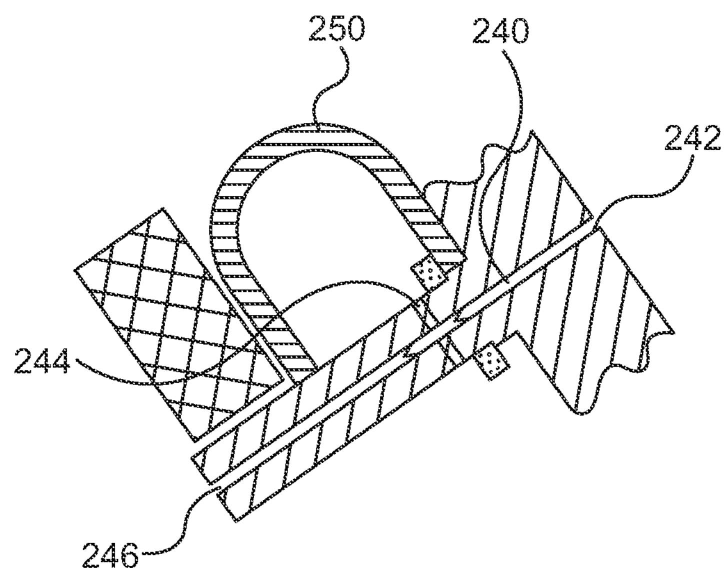
FIG. 9 shows a partial cross-section of a vacuum pump according to a third embodiment of the present invention.

In the embodiment shown in FIG. 9, a one-way valve 240 extends through a toroid 250. The one-way valve 240 includes an intake 242 to receive fluid from an external source, an inlet 244 to receive fluid from the toroid 250 upon compression of the toroid 250 and an outlet 246 through which the transferred fluid is expelled.

Figure 10:
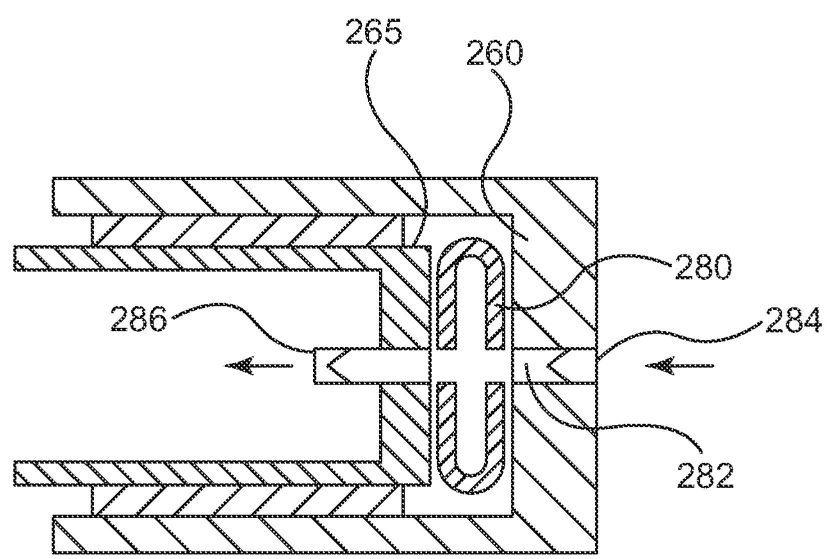
FIG. 10 shows a partial cross-section of a vacuum pump according to a fourth embodiment of the present invention.

The embodiment shown in FIG. 10 is similar to the embodiments shown in FIGS. 8 and 9, except that it includes an elastomeric structure 280, which is not toroidal in shape, positioned between an interior of the housing 260 and a reciprocating shaft 265. The elastomeric structure 280 includes an one-way valve 282, including an inlet 284 and an outlet 286, which extends approximately through the center of the elastomeric structure 280 to transfer fluid into and out of the elastomeric structure 280 upon compression/expansion.

Figure 11:
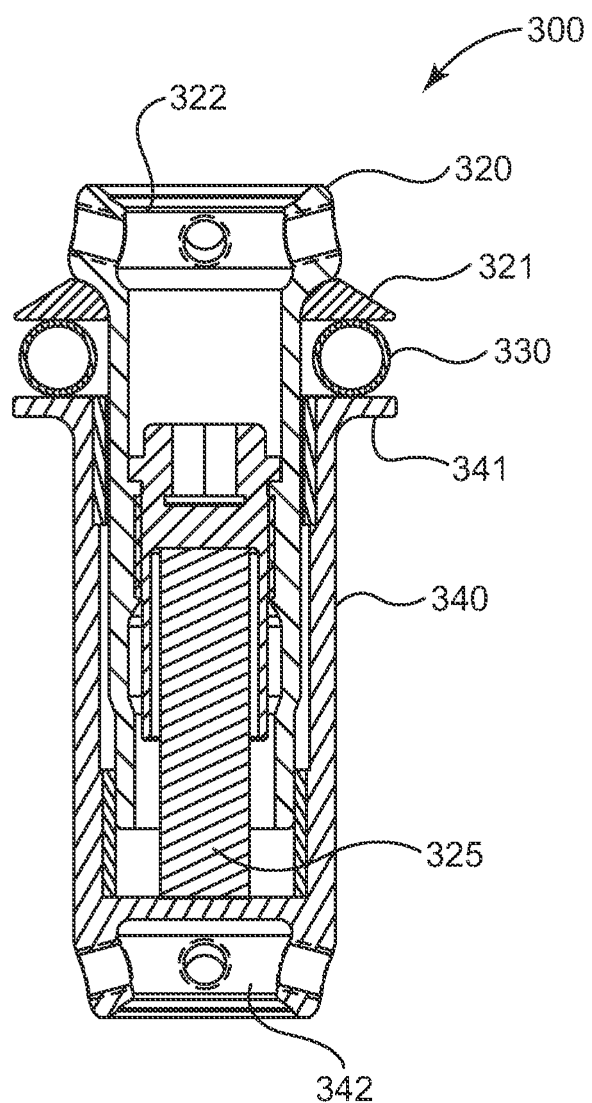
FIG. 11 shows a cross-section of a vacuum pump according to a fifth embodiment of the present invention.

FIG. 11 shows a pump 300 including a shaft 320 positioned within a housing 340. The shaft 320 and the housing 340 include mounting structures 322, 342, respectively, for connection to other prosthetic components. An elastomeric toroid 330 is positioned about the shaft 320 and is sandwiched between the shaft 320 and the housing 340 within flanges 321, 341, respectively, on the outer diameter of each tube. A resilient member 325 is coupled to the shaft 320 and positioned to contact the housing 340. Upon application of the compression force, the shaft 320 and housing 340 move relative to each other, compressing the toroid 330 and the resilient member 325. Upon release of the force, the resilient member 325 returns the shaft 320 to its initial position, allowing the toroid 330 to re-expand. This embodiment allows for a reduced wall thickness for toroid 300 because the resilient member 325 is capable of providing the primary return force.

Figure 12:
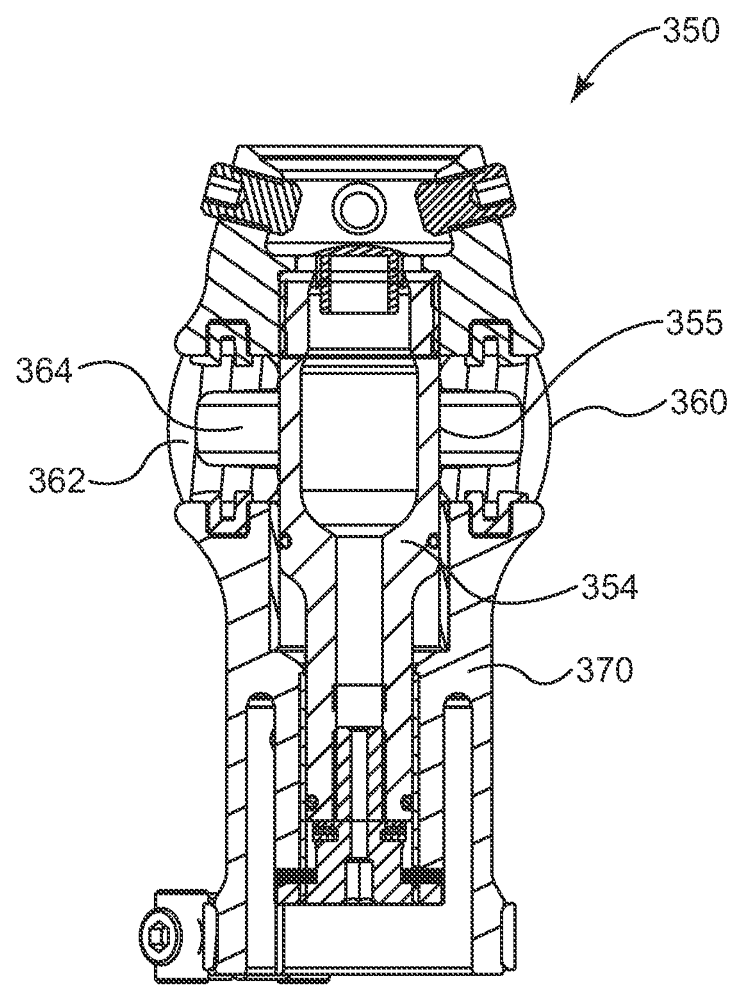
FIG. 12 shows a cross-section of a vacuum pump according to a sixth embodiment of the present invention.
Figure 13:
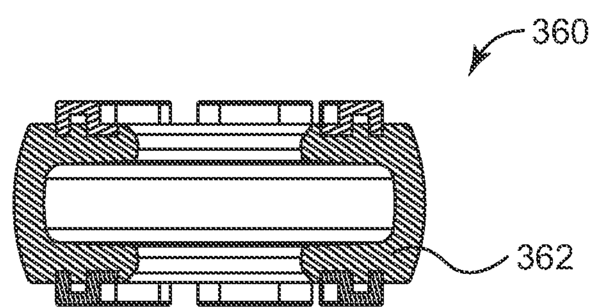
FIG. 13 shows a cross-section of a resilient portion of the vacuum pump of FIG. 12.

FIGS. 12 and 13 show a pump 350, which is very similar to the pump 100 shown in FIGS. 1-7, However, the pump 350 includes an elastomeric structure 360 that does not include an inner wall. Instead, the structure 360 is formed with a generally 'C' shaped outer wall 362 that seals against an outer surface 355 of the shaft 354 to form a hollow internal cavity 364. The structure 360 remains sealed with the outer shaft surface 355 even as the shaft 354 moves relative to the structure 360 and the housing 370.

Figure 14:
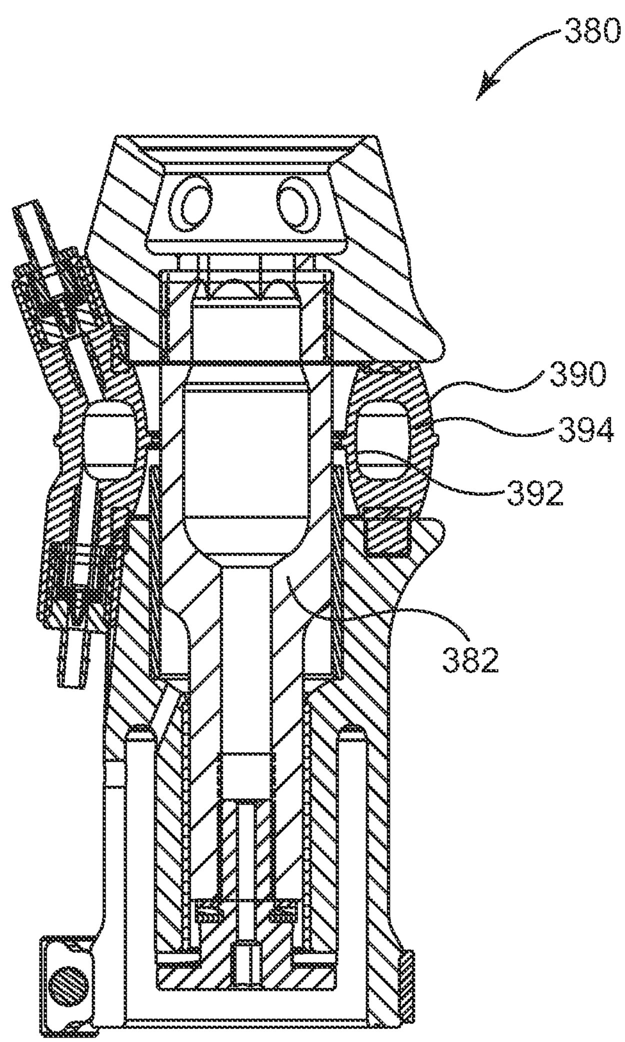
FIG. 14 shows a vacuum pump according to a seventh embodiment of the present invention.

FIG. 14 shows a pump 380, which is also similar to the pump 100 shown in FIGS. 1-7. However, pump 380 includes a toroid 390 having an internal wall 392 that, due to a thickness differential, is bowed inwardly toward the shaft 382 and away from the outer wall 394. As a result, the inner wall 392 requires a thickness that is less than the thickness of the outer wall 394, in order to achieve the desired rotational, compression and expansion resilience of the toroid 390.

Figure 15:
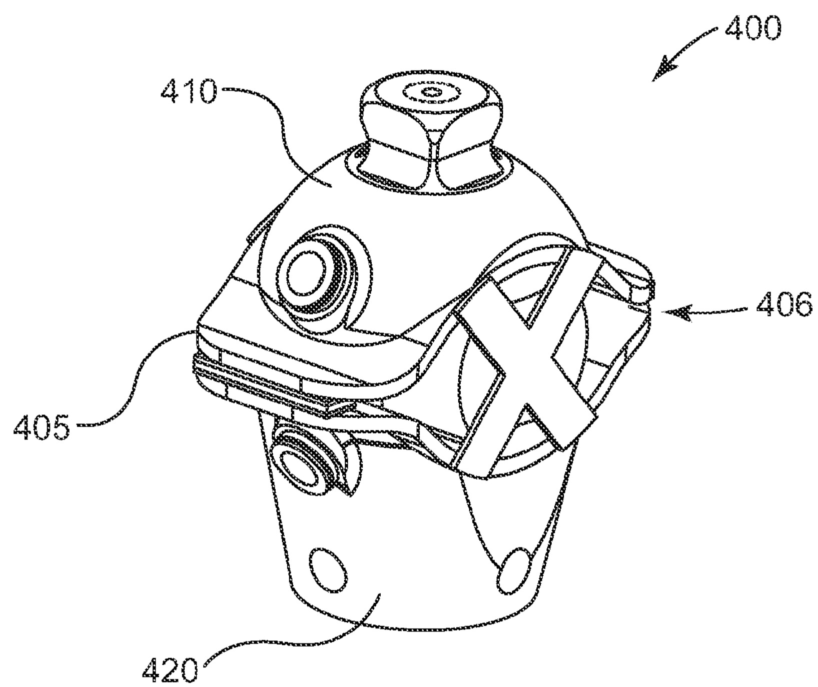
FIG. 15 shows a vacuum pump according to an eighth embodiment of the present invention.
Figure 16:
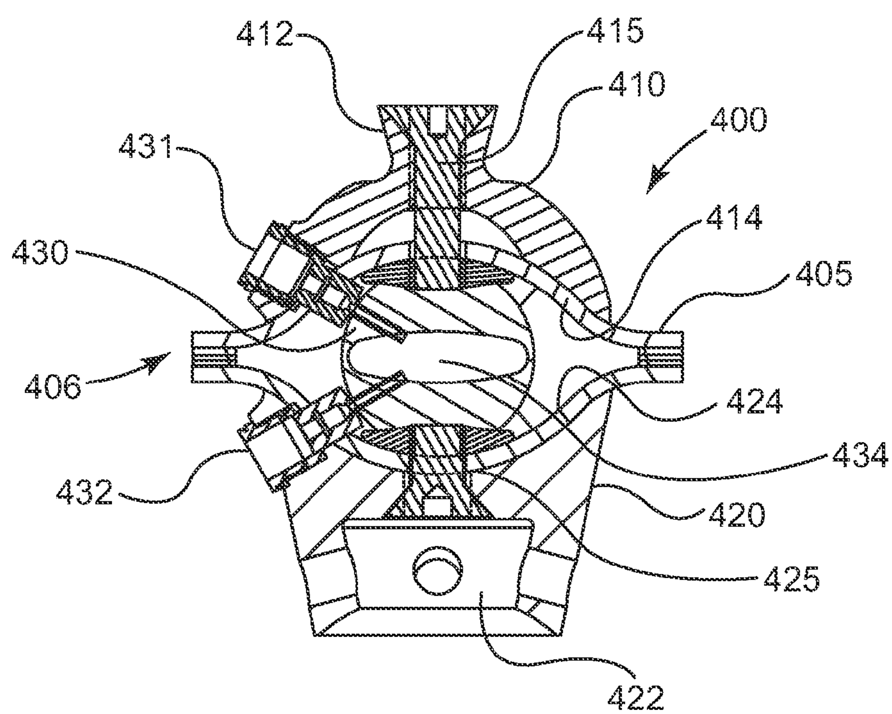
FIG. 16 shows a cross-section of the vacuum pump of FIG. 15.

FIGS. 15 and 16 show a pump 400, which does not include a shaft reciprocating within a housing. Instead the pump 400 includes a housing 405 having a top connecting component 410 and a bottom connecting component 420. As shown, the top connecting component 410 includes a pyramid connector 412, and the bottom connecting component 420 includes a coupler 422 for receiving a pyramid connector. A bottom element 414 of the top component 410 is configured to engage a top element 424 of the bottom component 420 forming an eye-shaped spring portion 406 within which a resilient hollow member 430 is positioned.

The resilient member 430 performs a similar function to the toroid in the above described embodiments. Intake and outlet one-way check valves 431, 432 are positioned in fluid connection with the hollow interior space 434 of member 430. Both the top component 410 and the bottom component 420 include connecting members 415, 425, respectively, that engage the resilient member 430 and transfer compression forces to it. When the pump 400 is subjected to a compression force, the top component 420 and the bottom component 420 move relative to each other causing compression of the resilient member 430 and transfer of fluid from the interior space 434. Upon removal of the compression force, the eye-shaped spring portion 406 aids in the expansion of the resilient member 430, transferring fluid out of a fluidly connected vessel and into the interior space 434.

Figure 17:
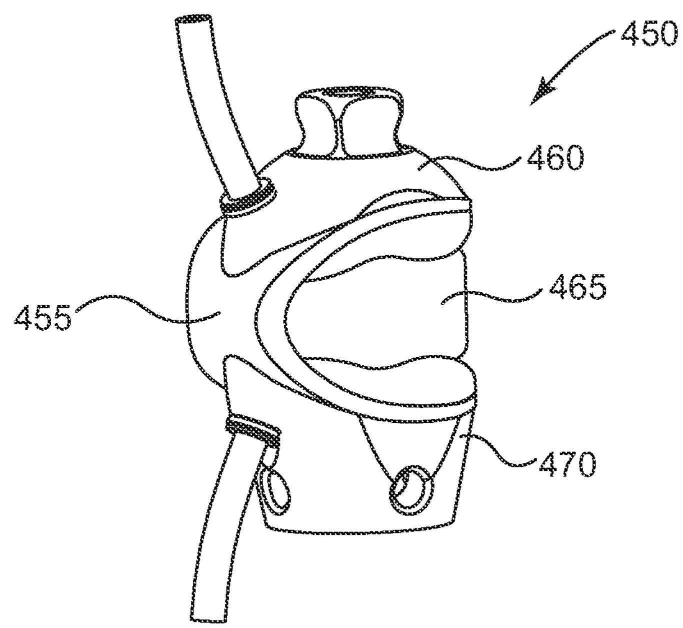
FIG. 17 shows a vacuum pump according to an ninth embodiment of the present invention.
Figure 18:
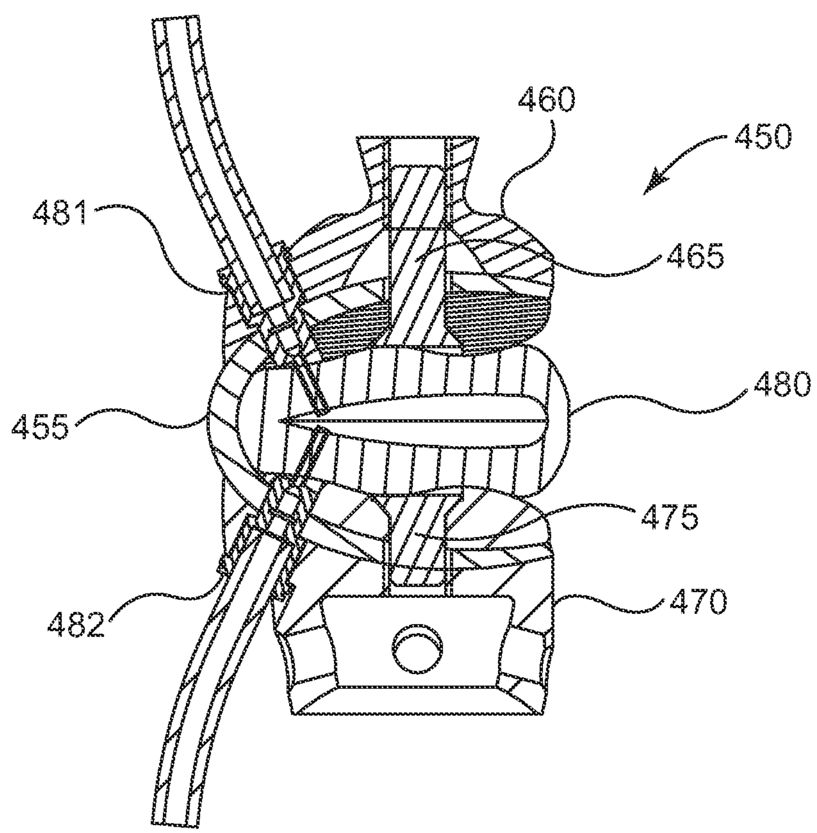
FIG. 18 shows a cross-section of the vacuum pump of FIG. 17.

FIGS. 17 and 18 show a pump 450 similar to the pump shown in FIGS. 15 and 16. A hollow resilient member 480 is positioned within a spring portion 455 formed between top and bottom connecting components 460, 470. Top and bottom connecting members 465, 475 engage the resilient member 480, and intake and outlet valves 481, 482 are in fluid connection with an interior space 484. Instead of an eye-shaped spring portion, the spring portion 455 is generally 'C' shaped and formed of a single component. As with the eye-shaped spring, the C-spring 455 aids during expansion of the resilient member 480 after removal of a compression force.

Figure 19:
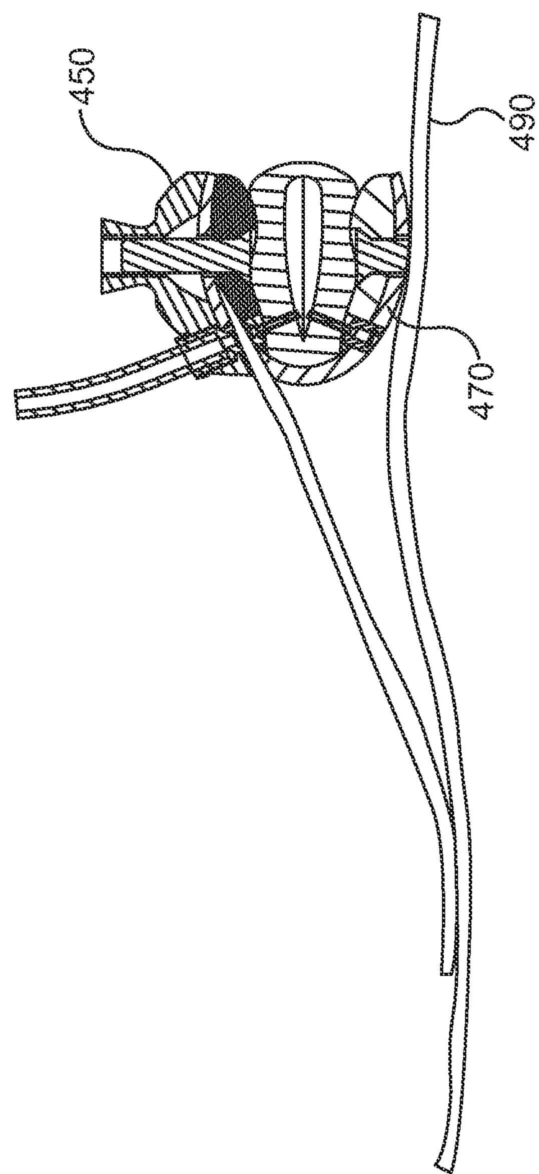
FIG. 19 shows the vacuum pump of FIGS. 17 and 18 incorporated into a prosthetic foot.

FIG. 19 shows the pump 450 positioned within a prosthetic foot 490. The bottom component 470 in this embodiment includes structure for positioning and coupling directly to the prosthetic foot 490. As shown, the pump 450 is provided in the heel portion of the foot 490, such that the compression force is applied to the pump 450 upon heel strike during the walking cycle.

Figure 20:
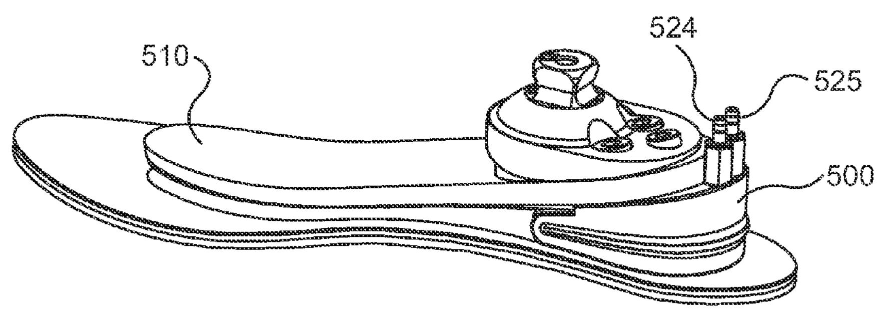
FIG. 20. shows a vacuum pump according to an tenth embodiment of the present invention incorporated into a prosthetic foot.
Figure 21:
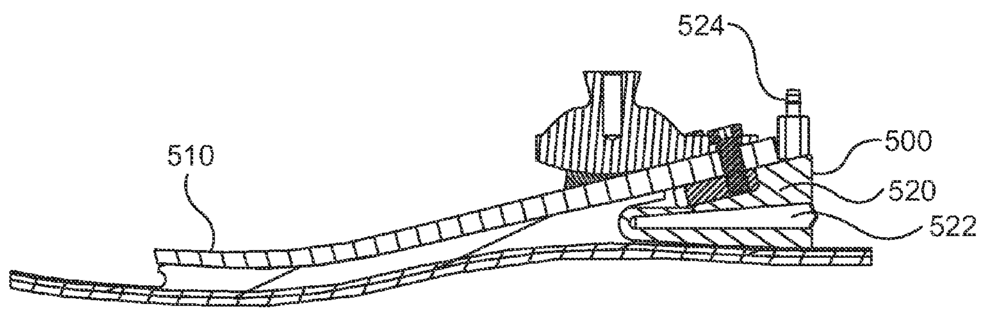
FIG. 21. shows a cross-section of the vacuum pump and prosthetic foot of FIG. 19.

FIGS. 20 and 21, also show a pump 500 positioned within the heel portion of a prosthetic foot 510. The pump 500 includes a resilient wedge component 520 having a hollow internal reservoir 522 in fluid connection with intake and outlet valves 524, 525. As with the other embodiments, a compression force, primarily applied during heel strike, compresses the resilient wedge 520 forcing fluid from the hollow internal space 522. Upon release of the force, the wedge 520 expands drawing fluid from a fluidly connected vessel. In this embodiment, the spring characteristics of the prosthetic foot 510 itself aid in the expansion of the wedge 520.

Figure 22:
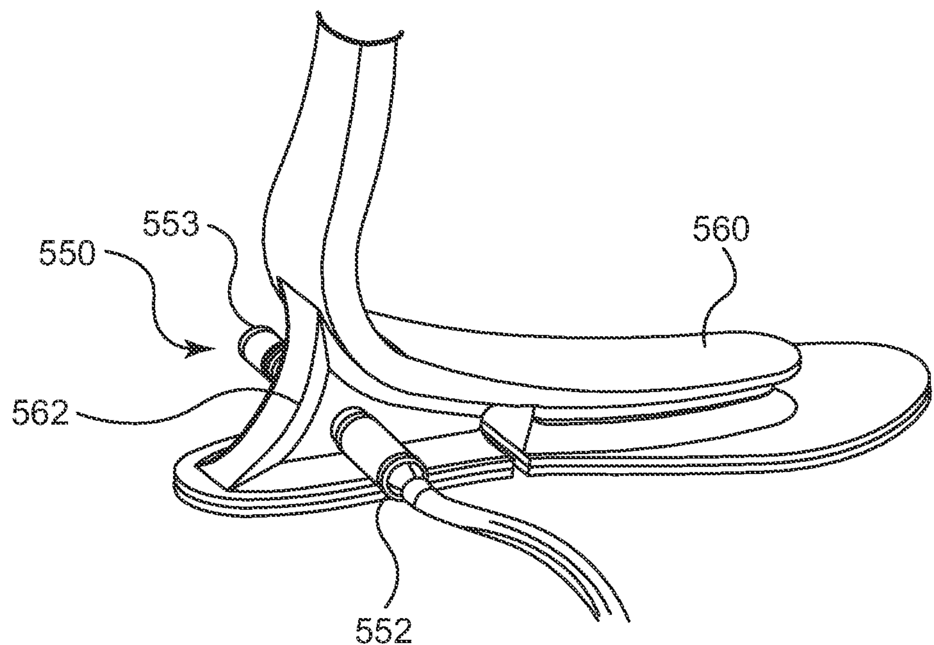
FIG. 22. shows a vacuum pump incorporated into a prosthetic foot according to an eleventh embodiment of the present invention.
Figure 23:
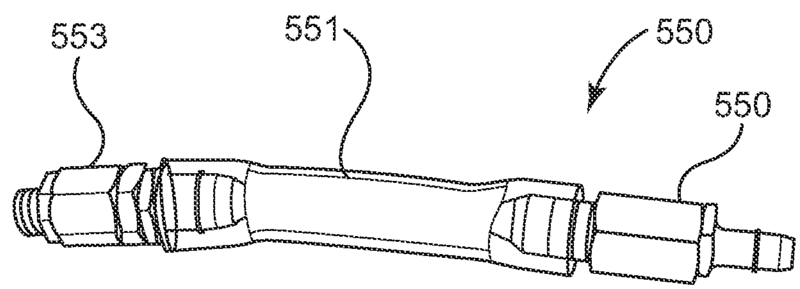
FIG. 23 shows the vacuum pump for incorporation into a prosthetic foot according to FIG. 22.

FIGS. 22 and 23, show a pump 550 again positioned in the heel portion of a prosthetic foot 560 having a resilient heel wedge 562. In this embodiment, the pump 550 is formed from a resilient cylinder 551 having intake and outlet valves 552, 553, respectively, positioned axially at opposite ends of the cylinder 551. The resilient cylinder 551 is received within the resilient heel wedge 562, such that a compression force is applied to the cylinder 551 during walking, especially at heel strike. In this case, the resilient heel wedge 562 not only transmits the compression force to the pump 550, but also aids in expansion of the resilient cylinder 551 to draw fluid from a fluidly connected vessel.

The vacuum pump of the present invention basically includes a resilient hollow member fluidly connected to intake and outlet valves. This resilient member is positioned within a structure having at least two surfaces that move relative to each other in a reciprocating manner. The resilient member repeatedly compresses and expands between the two surfaces due to the application and removal of a compression force applied to the pump. Each compression forces fluid out of the hollow internal space within the resilient member and each expansion draws fluid back into the internal space through the intake valve. When the intake valve is fluidly connected to a vessel, the compressive action of the pump will draw fluid out of the vessel.

The invention claimed is:

1. A prosthetic device for attachment to a residual limb, comprising:

a vacuum pump including:

a compressible elastomeric member alone forming an enclosed internal reservoir containing a volume of fluid;

an outlet port positioned on the external surface of the elastomeric member and providing fluid communication between the internal reservoir and a fluid sink; and an inlet port positioned on the external surface of the elastomeric member and providing fluid communication between the internal reservoir and a fluid source;

a first support member having a proximal end configured for attachment to the residual limb and a distal end coupled to a first side of the elastomeric member;

a second support member having a proximal end coupled to a second opposing side of the elastomeric member, wherein at least one of the first and second support members is adapted to apply a compression force along, and a rotational force about, a longitudinal axis extending through the elastomeric member;

wherein upon applying the compression force to the elastomeric member along the longitudinal axis, fluid flows from the internal reservoir to the fluid sink and upon removal of the compression force, fluid flows from the fluid source to the internal reservoir, and wherein upon applying the rotational force about the longitudinal axis, the elastomeric member exerts a counter-rotational force.

2. The prosthetic device of claim 1 wherein the second support member is configured for attachment to an additional prosthetic component.

3. A prosthetic device comprising:

an elongated lower pylon of the prosthetic device;

an elongated upper pylon of the prosthetic device adapted to move axially and rotationally with respect to said lower pylon, wherein a longitudinal axis of the upper pylon and a longitudinal axis of the lower pylon are maintained in a generally collinear alignment;

a toroid-shaped resilient compressible elastic member having an upper end coupled to the upper pylon and a lower end coupled to the lower pylon to resist the axial and rotational movement of the lower pylon, wherein the elastic member forms an enclosed internal reservoir containing a volume of fluid;

an outlet port providing fluid communication between the internal reservoir and a fluid sink;

an inlet port providing fluid communication between the internal reservoir and a fluid source; and a shaft portion extending from the upper pylon, through an opening in the elastic member and into a compartment of the lower pylon;

wherein upon applying a weight force to the elastic member by the upper pylon along the longitudinal axes, the upper pylon moves relative to the lower pylon to compress the elastic member such that fluid flows from the internal reservoir to the fluid sink, and wherein upon applying an expansion force, the upper pylon moves relative to the lower pylon to expand the elastic member such that fluid flows from the fluid source to the internal reservoir.

4. The prosthetic device of claim 3 wherein the elastic member comprises a substantially continuous elastic wall enclosing the internal reservoir.

5. The prosthetic device of claim 4 wherein the wall of the elastic member is sufficiently resilient to apply the expansion force.

6. The prosthetic device of claim 3 wherein the outlet port and the inlet port are positioned on an outer surface of the elastic member.

7. The prosthetic device of claim 3 wherein the fluid sink and fluid source are external to the prosthetic device.

8. The prosthetic device of claim 3 wherein the fluid is a gas.

9. A prosthetic device comprising:

a toroid-shaped member including an upper side, a lower side and a continuous elastomeric wall forming an enclosed reservoir containing a volume of fluid, the toroid-shaped member having a longitudinal axis extending through the upper side and lower side;

a first support member having a proximal end configured for attachment to an outer surface of a residual limb, and a distal end coupled to the upper side of the toroid-shaped member;

a second support member having a proximal end coupled to the lower side of the toroid-shaped member;

an outlet port positioned on the toroid-shaped member to provide fluid flow out of the enclosed reservoir;

an inlet port positioned on the toroid-shaped member to provide fluid flow into the enclosed reservoir;

wherein upon applying a compression force along the longitudinal axis, the toroid-shaped member is compressed so that fluid flows out of the enclosed reservoir, and upon removal of the compression force, the toroid-shaped member expands so that fluid flows into the enclosed reservoir;

wherein upon rotation of the first support member relative to the second support member about the longitudinal axis, the toroid-shaped member exerts a counter-rotational force.

10. The prosthetic device of claim 9, wherein the elastomeric wall includes an outer wall having an outer circumference and an inner wall having an inner circumference and wherein the inner circumference defines an opening extending from the upper side through the lower side of the toroid-shaped member.

11. The prosthetic device of claim 10 wherein the first support member comprises a shaft that extends through the opening and the second support member comprises a housing into which a portion of the shaft extends.

12. The prosthetic device of claim 11 wherein the housing comprises an interior compartment configured such that the shaft is allowed to move along the longitudinal axis within the interior compartment during compression and expansion of the toroid-shaped member.

13. A prosthetic device comprising:

an elongated lower pylon of the prosthetic device;

an elongated upper pylon of the prosthetic device adapted to move axially and rotationally with respect to said lower pylon, wherein a longitudinal axis of the upper pylon and a longitudinal axis of the lower pylon are maintained in a generally collinear alignment;

a toroid-shaped resilient compressible elastic member having an upper end coupled to the upper pylon and a lower end coupled to the lower pylon, wherein the resilient compressible elastic member applies spring forces that act against both axial movement and rotational movement of the lower pylon, and wherein the elastic member alone forms an enclosed internal reservoir containing a volume of fluid;

an outlet port providing fluid communication between the internal reservoir and a fluid sink;

an inlet port providing fluid communication between the internal reservoir and a fluid source; and a shaft portion extending from the upper pylon, through an opening in the elastic member and into a compartment of the lower pylon;

wherein upon applying a compression force along the longitudinal axes, the upper pylon moves relative to the lower pylon to compress the elastic member such that fluid flows from the internal reservoir to the fluid sink, and wherein upon applying an expansion force, the spring force of the elastic member moves the upper pylon relative to the lower pylon such that fluid flows from the fluid source to the internal reservoir.

* * * * *